United States Patent
Frély et al.

(10) Patent No.: US 9,517,061 B2
(45) Date of Patent: Dec. 13, 2016

(54) THREAD ANCHOR

(71) Applicants: Stryker European Holdings I, LLC, Kalamazoo, MI (US); Woodwelding AG, Stansstad (CH)

(72) Inventors: Jean-Claude Frély, Bienne (CH); Thomas Knecht, Baden (CH); Astrid Bordush, Ottawa (CA)

(73) Assignee: Stryker European Holdings I, LLC, Kalamazoo, MI (US)

( * ) Notice: Subject to any disclaimer, the term of this patent is extended or adjusted under 35 U.S.C. 154(b) by 84 days.

(21) Appl. No.: 14/402,566

(22) PCT Filed: May 21, 2013

(86) PCT No.: PCT/EP2013/060349
§ 371 (c)(1),
(2) Date: Nov. 20, 2014

(87) PCT Pub. No.: WO2013/174779
PCT Pub. Date: Nov. 28, 2013

(65) Prior Publication Data
US 2015/0142051 A1 May 21, 2015

(30) Foreign Application Priority Data

May 21, 2012 (DE) .............. 20 2012 005 004 U

(51) Int. Cl.
*A61B 17/04* (2006.01)
*A61B 17/00* (2006.01)

(52) U.S. Cl.
CPC ..... *A61B 17/0401* (2013.01); *A61B 17/00491* (2013.01); *A61B 2017/005* (2013.01);
(Continued)

(58) Field of Classification Search
CPC .............. A61B 17/04; A61B 2017/00955; A61B 2017/0409; A61B 17/68; A61B 17/0642; A61B 2017/0414; A61B 17/320068; A61B 2017/0619; A61B 2017/0454; A61F 2002/30065; A61F 2210/0071; A61F 2002/0888; A61F 2002/4683; B29C 65/08
(Continued)

(56) References Cited

U.S. PATENT DOCUMENTS

| 5,993,458 A | 11/1999 | Vaitekunas et al. |
| 2007/0191957 A1* | 8/2007 | Anderson .......... A61B 17/0401 623/17.16 |

(Continued)

FOREIGN PATENT DOCUMENTS

| WO | 0002489 A1 | 1/2000 |
| WO | 02069817 A1 | 9/2002 |
| WO | 2008/034276 A2 | 3/2008 |

OTHER PUBLICATIONS

International Search Report for Application No. PCT/EP2013/060349 dated Aug. 19, 2013.

*Primary Examiner* — Katherine M Shi
(74) *Attorney, Agent, or Firm* — Lerner, David, Littenberg, Krumholz & Mentlik, LLP

(57) ABSTRACT

A method and a device for anchoring a suture to an object includes a shuttle and a pin made of a material which can be liquefied by means of ultrasonic vibrations. A suture is attached to a rear end of the pin. The shuttle has a shuttle body, a shuttle arm and a suture reception, wherein the shuttle arm is suitable for releasably holding the pin in a predetermined position relative to the shuttle body such that the pin can be reliably introduced into a hole in an object.

11 Claims, 3 Drawing Sheets

(52) U.S. Cl.
CPC ............... *A61B 2017/00955* (2013.01); *A61B 2017/0403* (2013.01); *A61B 2017/0404* (2013.01); *A61B 2017/0409* (2013.01)

(58) Field of Classification Search
USPC .............................. 623/11.11; 606/104, 232
See application file for complete search history.

(56) References Cited

U.S. PATENT DOCUMENTS

| | | | | |
|---|---|---|---|---|
| 2007/0235359 | A1* | 10/2007 | Ruffieux | A61B 17/0401 206/339 |
| 2007/0265704 | A1* | 11/2007 | Mayer | A61B 17/0469 623/11.11 |
| 2007/0270854 | A1* | 11/2007 | Li | A61B 17/0401 606/232 |
| 2008/0125815 | A1* | 5/2008 | Heaven | A61B 17/0401 606/308 |
| 2009/0018581 | A1* | 1/2009 | Anderson | A61B 17/0401 606/232 |
| 2010/0023057 | A1* | 1/2010 | Aeschlimann | A61B 17/0401 606/246 |

\* cited by examiner

THREAD ANCHOR

CROSS-REFERENCE TO RELATED APPLICATIONS

The present application is a national phase entry under 35 U.S.C. §371 of International Application No. PCT/EP2013/060349 filed May 21, 2013, published as WO 2013/174779 A1, which claims priority from DE Patent Application No. 20 2012 005 004.4 filed May 21, 2012, the disclosures of which are hereby incorporated herein by reference.

FIELD OF THE INVENTION

The invention relates to a method and to a device for anchoring a suture to an object. More particularly, the invention relates to a method and to a device for anchoring a suture to an object using ultrasonic vibrations.

BACKGROUND OF THE INVENTION

In order to attach a suture to an object, more particularly to a surface of an object, a suture can be clamped for example by means of a screw between the screw and the object. However, this option has the disadvantage that the suture cannot be reliably attached or might be damaged.

Alternatively, it is known to securely connect a suture to a screw beforehand and to then screw said screw into a hole in an object. However, so long as the free end of the suture can move freely while the screw is being screwed in, handling a screw-suture combination of this type is complicated. In order to overcome this disadvantage, there are systems in which a screw is provided, together with at least one suture, such that it is releasably connected to a suitable tool in a preassembled manner. However, this variant is expensive as a result of the tool to be supplied with each screw.

SUMMARY OF THE INVENTION

It is an object of the invention to provide a method and a device for anchoring a suture to an object. Additional objects can be considered to be ensuring improved handling of the device and reliable and secure anchoring of a suture to an object.

These and additional objects are achieved by the subject matter of each of the independent claims. Additional embodiments can be found in each of the dependent claims.

In general, a device for anchoring a suture to an object comprises a pin. The pin can be produced from a material, for example a suitable polymer, which can be liquefied by means of ultrasonic vibrations. Furthermore, at least one suture can be connected to the pin, wherein the at least one suture can be attached to a rear end of the pin. The pin can have for example a diameter of 2.8 mm and a length of 7 mm.

The pin comprises a body having a longitudinal extension (length) and a transverse extension (cross section, diameter), wherein the pin can be introduced or inserted preferably in the direction of the longitudinal extent into a recess or opening in an object. To make the introduction easier, the front end of the pin can be tapered or bevelled. The rear end of the pin is thus the end which is at the rear of the pin in the introduction direction.

By fixing the suture to the rear end, it can be ensured that the suture is not damaged during the introduction of the pin and thus during the anchoring. It should be noted that the suture can be securely connected to the pin for example by embedding during the production of the pin, and that the suture can also, however, be guided through a recess (a cross hole, a suture eyelet) or can be fixed to the pin by means of a hook or a clamping yoke.

According to one embodiment, the device further comprises a shuttle having a shuttle body and at least one shuttle arm, wherein the shuttle arm is suitable for releasably holding the pin in a predetermined position relative to the shuttle body.

According to one embodiment, the shuttle can further comprise a suture reception for receiving the suture.

By means of a shuttle, a pin can be held together with a suture such that the pin (even if the pin is relatively small) can be reliably introduced into a hole in an object, without there being any conflict with the suture which is connected to the pin.

According to another embodiment, the device further comprises a protection cap which can be connected to the shuttle such that a pin held by the shuttle arm is covered. Covering the pin with a protection cap can be advantageous in particular in the field of medical applications, since this can prevent not only damage to the pin but also contamination during the transportation of the pin (on the shuttle).

According to another embodiment, the device further comprises an ultrasonic applicator having a sonotrode. The ultrasonic applicator can be releasably connected to the shuttle such that the tip of the sonotrode can be brought into contact with the pin held by the shuttle arm.

In other words, a shuttle with a pin can be arranged on an ultrasonic applicator such that the tip of the sonotrode is in contact with the rear end of the pin. Thus the pin which is held by the shuttle, which in turn is connected to the ultrasonic applicator, can be securely introduced into a hole in an object and can be liquefied or at least softened by means of ultrasonic vibrations which can be generated by the ultrasonic applicator so that the material of the pin can be reliably connected to the material of the object or can be anchored thereto.

According to one embodiment, the ultrasonic applicator comprises a latch, wherein the shuttle can be locked on the ultrasonic applicator by means of the latch. The latch can furthermore be configured such that a protection cap can also be releasably connected to the ultrasonic applicator.

According to one embodiment, the shuttle of the device comprises two shuttle arms which are arranged such that the pin can be held between the two shuttle arms, wherein the shuttle arms can be configured such that the tip of a sonotrode can also be arranged between the shuttle arms. Furthermore, a suture reception can be provided on the shuttle body. If two sutures are connected to the pin, each suture can be guided along a shuttle arm towards the suture reception and received therein as long as the pin is held by the shuttle arms.

According to a further embodiment, the device further comprises a needle which can be attached to a free end of the suture.

For example it is conceivable to attach two sutures to a surface of a bone. For this purpose, a pin comprising two sutures can be inserted in a hole which has been made in the bone in advance. By means of ultrasonic vibrations, the material of the pin can then be melted at least in part so that the pin is securely anchored in the bone. In this way, the two sutures are anchored to the bone. The sutures can be used to attach soft tissue structures to the bone. The attachment of the soft tissue structures can additionally be simplified if at least one needle is fixed to a free end of a suture. After the soft tissue structures have been attached, the needle, together with an excess length of the suture, can be cut off and thus removed.

Alternatively, it is conceivable to attach one or more sutures to an object made of stone, earthenware, wood or a plastics material.

The above-described aspects and additional aspects, features and advantages of the invention can also be found in the examples in the embodiments, which are described below with reference to the accompanying drawings.

BRIEF DESCRIPTION OF THE DRAWINGS

It should be noted that the illustrations in the drawings are merely schematic and are not intended to give any indication of possible proportions. In the drawings, identical or like aspects are given the same reference numerals.

DETAILED DESCRIPTION OF AN EMBODIMENT

Figure 1:
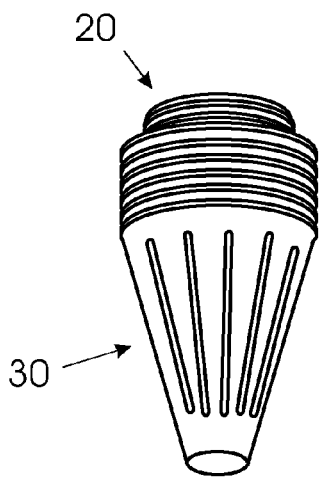
FIG. 1 shows a shuttle comprising a protection cap.

FIG. 1 shows a protection cap 30 in which a shuttle 20 is arranged. The protection cap 30 is formed by a hollow body which comprises an annular region on one side and a frustoconical region on the other side. The external surfaces of the protection cap comprise grooves or ribs which make it easier to hold and handle the protection cap. The protection cap 30 can also be configured with a different external shape as long as a cavity is formed which is suitable for receiving a shuttle together with a pin.

Figure 2:
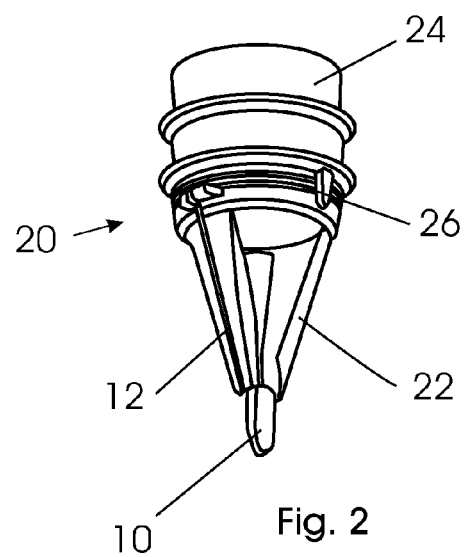
FIG. 2 shows a shuttle together with a pin comprising a suture.

FIG. 2 shows a shuttle 20 which comprises an annular shuttle body 24, two shuttle arms 22 and a suture reception 26. A pin 10, to the rear end of which at least one suture 12 is attached, is arranged and held between the ends of the shuttle arms 22. A suture 12 is guided along a shuttle arm 22 towards the shuttle body 24 and received in the suture reception 26. The suture reception 26 can be configured such that a free end of a suture can be clamped in and thus secured. Moreover, the suture reception 26 can be configured such that a needle (not shown), which is fixed at the free end of the suture, can also be received.

Figure 3:
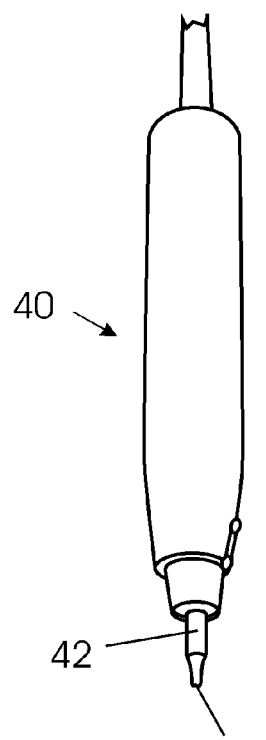
FIG. 3 shows an ultrasonic applicator.

FIG. 3 shows an ultrasonic applicator 40 which comprises at one end a sonotrode 42 having a sonotrode tip 44. The sonotrode 42 protrudes from the housing of the ultrasonic applicator 40. Inside the ultrasonic applicator, an ultrasonic generator (not shown) is accommodated, which is connected to the sonotrode 42 so that vibrations which are generated by the ultrasonic generator can be passed along to the sonotrode.

Figure 4:
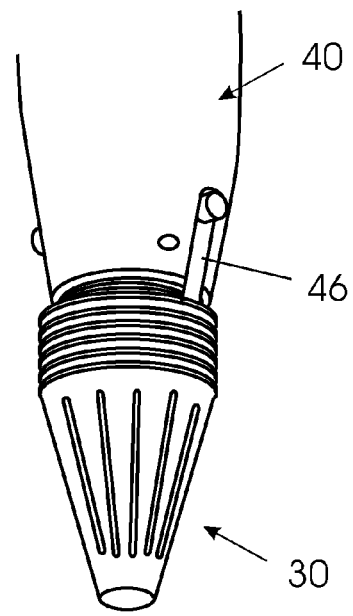
FIG. 4 shows a shuttle comprising a protection cap on an ultrasonic applicator.

In FIG. 4, a combination of the shuttle 20 and the protection cap 30 is attached to the ultrasonic applicator 40. On the ultrasonic applicator, a latch 46 is provided which is configured such that the protection cap 30 and the shuttle can be releasably locked on the housing of the ultrasonic applicator by means of the latch 46. For example the latch 46 can be actuatable such that the protection cap 30, but not the shuttle 20, can be removed from the ultrasonic applicator 40.

Figure 5:
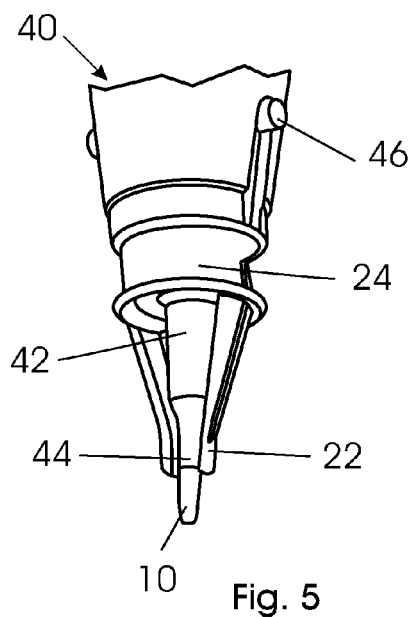
FIG. 5 shows a shuttle comprising a pin on an ultrasonic applicator.

FIG. 5 shows a state in which a shuttle without a protection cap is connected to the ultrasonic applicator 40. In this drawing, it can be seen that the shuttle body 24 can be locked on the ultrasonic applicator by the latch 46. Furthermore, it can be seen that the shuttle arms 22 hold the pin 10 relative to the ultrasonic applicator and thus to the sonotrode 42 such that the tip of the sonotrode 44 is in contact with the rear end of the pin 10. This contact is necessary so that vibrations of the sonotrode can be transmitted to the material of the pin.

Figure 6:
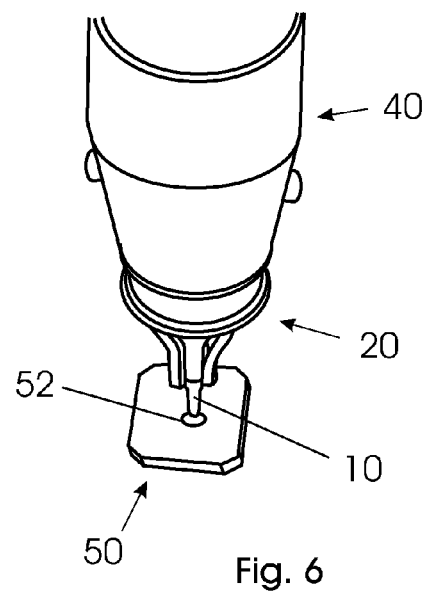
FIG. 6 shows how a pin is inserted in a hole.

FIG. 6 shows a situation in which the pin 10 can be held oriented towards a recess 52 in an object 50. The recess 52 can be a hole or a suitable opening, wherein the pin 10 has a diameter or a cross-sectional shape which corresponds to the diameter of the hole or the shape of the opening.

As soon as the pin 10 is introduced or inserted into the recess 52, the material of the pin can be melted or at least softened by ultrasonic vibrations so that the material of the pin 10 fills up the recess 52, including the surface roughness, the pin 10 thereby being securely anchored in the recess.

It should be noted at this point that the recess 52 can also be configured to be for example angular, star-shaped or oval. The fact that the material of the pin 10 is melted allows a pin having a complementary shape to fill up the recess 52, even if the cross-sectional shape of the pin does not coincide with that of the recess. This aspect is also made easier in that the pin is merely pushed into the recess, i.e. the pin is only moved in the longitudinal or introduction direction, and does not have to be twisted, as with a screw.

Figure 7:
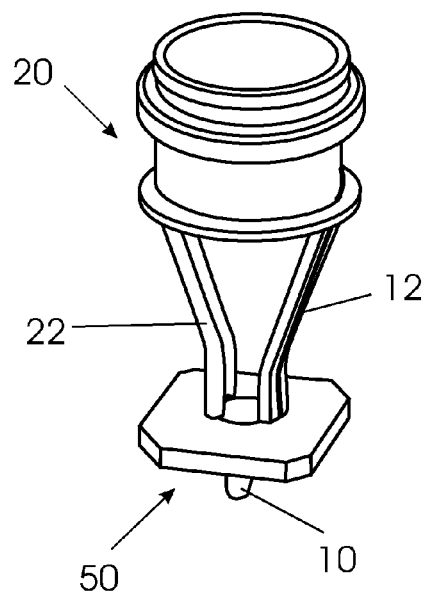
FIG. 7 shows a shuttle comprising a pin anchored in a hole.

FIG. 7 shows a state in which the pin 10 is already securely anchored in the object 50 and the ultrasonic applicator comprising the sonotrode has been removed. In this situation, the suture 12 can be released in the suture reception so that the shuttle 20 can be separated from the pin and the suture.

Figure 8:
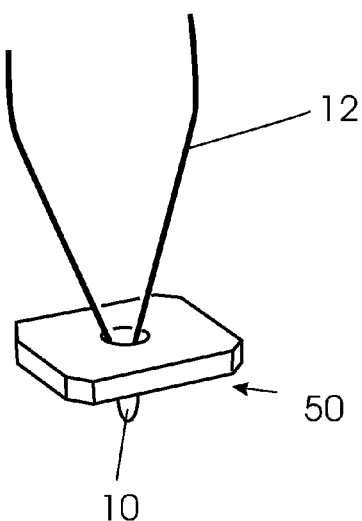
FIG. 8 shows a pin, comprising two sutures, anchored in a hole.

FIG. 8 shows a pin 10 which is anchored in an object 50, wherein two sutures 12 protrude at the rear end of the pin 10. It can be seen here that it is possible to anchor sutures to an object such that the surface of the object 50 can be flush with the rear end of a pin.

Figure 9:
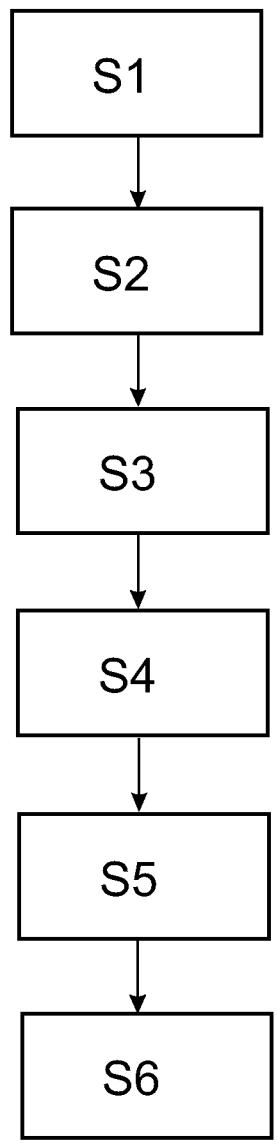
FIG. 9 is a flow chart which shows steps of a method for anchoring a suture to an object.

The flow chart in FIG. 9 illustrates steps of a method for anchoring a suture to an object. It should be noted that the steps which are described with reference to the method and also to FIG. 9 are main steps, wherein said main steps can be differentiated and/or subdivided into sub-steps. Moreover, there can be additional sub-steps between the main steps. A sub-step is only mentioned, however, when said step is important for the comprehension of the principles of the method according to the invention.

In step S1, a pin is provided, to the rear end of which a suture is attached, wherein the pin is produced from a material which can be liquefied by means of ultrasonic vibrations.

In step S2, the pin is held by means of a shuttle. In other words, the pin is releasably attached to the shuttle.

In step S3, the shuttle is connected to an ultrasonic applicator so that a tip of a sonotrode of the ultrasonic applicator can be brought into contact with the pin. If for example the tip of the sonotrode protrudes at a front end of the ultrasonic applicator, the shuttle can be fitted and optionally locked on the front of the ultrasonic applicator.

In step S4, the pin is introduced into a hole in an object. This means that the pin can be attached to the shuttle such that the tip of the pin protrudes. In this way, even a very small pin can be handled.

In step S5, the material of the pin is liquefied or at least softened by means of ultrasonic vibrations which can be generated by the ultrasonic applicator so that the pin is anchored to the object, for example due to the penetration of the material of the pin into cracks and pores in the object.

In step S6, after the pin has been anchored to the object, the suture can be released from a suture reception. The suture reception can be provided on the shuttle so that the suture in step S2 can be received in the suture reception and held therein in the steps S3 to S5 so that unintentional tangling and/or knotting can be prevented.

Whilst the invention has been illustrated and described in detail in the drawings and in the preceding description, illustrations and descriptions of this type are intended to be merely illustrative or given by way of example and to be non-restricting, so that the invention is not limited by the disclosed embodiment. Other variations of the disclosed embodiment can be understood by a person skilled in the art when implementing the claimed invention and brought about by a study of the drawings, the disclosure and the accompanying claims.

In the claims, the word "comprising" does not exclude other elements and the indefinite article "a" does not exclude a plurality.

The mere fact that certain features are mentioned in various dependent claims does not limit the subject matter of the invention. Any desired combinations of these features can also advantageously be used. The reference numerals in the claims are not intended to limit the scope of the claims.

LIST OF REFERENCE NUMERALS 10 pin
12 suture
20 shuttle
22 shuttle arm
24 shuttle body
26 suture reception
30 protection cap
40 ultrasonic applicator
42 sonotrode
44 tip of sonotrode
46 latch
50 object
52 recess

The invention claimed is:

1. A device for anchoring a suture to an object, comprising a pin, a suture and a shuttle, wherein the pin is produced from a material which can be liquefied by means of ultrasonic vibrations, and wherein the suture is securely connected at one end thereof to the pin, and wherein the shuttle comprises a shuttle body and at least one shuttle arm, wherein the shuttle arm is suitable for releasably holding the pin in a predetermined position relative to the shuttle body;
   an ultrasonic applicator, wherein the ultrasonic applicator comprises a sonotrode and wherein the ultrasonic applicator can be releasably connected to the shuttle such that the tip of the sonotrode can be brought into contact with the pin held by the shuttle arm; and
   wherein the ultrasonic applicator comprises a latch for locking the shuttle on the ultrasonic applicator.

2. The device according to claim 1, wherein the shuttle further comprises a suture reception for receiving the suture.

3. The device according to claim 1, further comprising a protection cap which can be connected to the shuttle such that the pin held by the shuttle arm is covered.

4. The device according to claim 1, wherein the shuttle comprises two shuttle arms which are arranged such that the pin can be held between the two shuttle arms, wherein the suture reception is provided on the shuttle body, and wherein two sutures are connected to the pin, wherein each suture is guided along a respective shuttle arm towards the suture reception and is received therein when the pin is held by the shuttle arms.

5. The device according to claim 1, further comprising a needle which is attached to a free end of the suture.

6. A method for anchoring a suture to an object, comprising the steps of:
   providing a pin, to the rear end of which a suture is attached, wherein the pin is produced from a material which can be liquefied by means of ultrasonic vibrations;
   holding the pin by means of a shuttle, the shuttle having a suture reception receiving the suture;
   connecting the shuttle to an ultrasonic applicator so that a tip of a sonotrode of the ultrasonic applicator can be brought into contact with the pin;
   introducing the pin into a hole in the object;
   liquefying the material of the pin by means of ultrasonic vibrations which can be generated by the ultrasonic applicator so that the pin is anchored to the object; and
   wherein the suture is released from the suture reception after the pin has been anchored to the object.

7. A device for anchoring a suture to an object comprising:
   a shuttle having a body;
   first and second arms having first ends coupled to the body and extending distally from the body, the first and second arms having second ends, the first and second arms extending at an angle with respect to the shuttle body so that the second ends are spaced closer together than the first ends;
   a pin releasably mounted intermediate the second end of each of the first and second arms, the pin made from a material which can be liquefied by ultrasonic vibrations;
   a first suture mounted on the body, the first and second arms guiding the first suture towards the pin for engagement therewith;
   further comprising an ultrasonic applicator, wherein the ultrasonic applicator comprises a sonotrode shaft and wherein the ultrasonic applicator can be releasably connected to the shuttle body such that a tip of the sonotrode shaft can be brought into contact with the pin held by the first and second arms; and
   wherein the ultrasonic applicator comprises a releasable latch engagable with the shuttle body for locking the shuttle body on the ultrasonic applicator.

8. The device according to claim 7, further comprising a protection cap connected to the shuttle such that the pin held by the first and second arm is covered.

9. The device according to claim 7 wherein the suture contact with the pin when the tip of the sonotrode is in contact with the pin.

10. The device according to claim 7, further comprising a needle which is attached to a free end of the suture.

11. The device according to claim 7 further comprising a second suture connected to the pin, the second suture guided by the second arm towards the pin.

* * * * *